United States Patent
Ferrari et al.

(10) Patent No.: US 9,868,757 B2
(45) Date of Patent: Jan. 16, 2018

(54) 5-β, 14-β-ANDROSTANE DERIVATIVES USEFUL FOR THE TREATMENT OF PROTEINURIA, GLOMERULOSCLEROSIS AND RENAL FAILURE

(71) Applicant: SIGMA-TAU INDUSTRIE FARMACEUTICHE RIUNITE S.p.A., Rome (IT)

(72) Inventors: Patrizia Ferrari, Varese (IT); Giuseppe Bianchi, Milan (IT); Mara Ferrandi, Milan (IT)

(73) Assignee: SIGMA-TAU INDUSTRIE FARMACEUTICHE RIUNITE S.P.A., Rome (IT)

( * ) Notice: Subject to any disclaimer, the term of this patent is extended or adjusted under 35 U.S.C. 154(b) by 0 days.

(21) Appl. No.: 14/931,083

(22) Filed: Nov. 3, 2015

(65) Prior Publication Data

US 2016/0251392 A1   Sep. 1, 2016

Related U.S. Application Data

(63) Continuation of application No. 13/258,728, filed as application No. PCT/EP2010/053571 on Mar. 18, 2010, now abandoned.

(30) Foreign Application Priority Data

Mar. 23, 2009   (EP) .................................... 09155834

(51) Int. Cl.
| | |
|---|---|
| *A61K 31/58* | (2006.01) |
| *C07J 17/00* | (2006.01) |
| *C07J 41/00* | (2006.01) |
| *C07J 43/00* | (2006.01) |

(52) U.S. Cl.
CPC ........... *C07J 17/00* (2013.01); *C07J 41/0038* (2013.01); *C07J 43/003* (2013.01)

(58) Field of Classification Search
CPC ....... C07J 17/00; C07J 41/0038; C07J 43/003
USPC .......................................................... 514/172
See application file for complete search history.

(56) References Cited

FOREIGN PATENT DOCUMENTS

| EP | 0 583 578 | 2/1994 |
|---|---|---|
| WO | 2007/118830 | 10/2007 |
| WO | 2007/118832 | 10/2007 |
| WO | 2007/147713 | 12/2007 |
| WO | 2008/148812 | 12/2008 |

OTHER PUBLICATIONS

Conway, et al. "Role of α-adducin DNA Polymorphisms in the Genetic Predisposition to Diabetic Nephropathy", Nephrology Dialysis Transplantation (2004), 19:2019-2024.
Ferrari, et al. "Rostafuroxin: An Ouabain Antagonist That Corrects Renal and Vascular Na+-K+-ATPase Alterations in Ouabain and Adducin-Dependent Hypertension", Am. J. Physiol Regul. Integr. Comp. Physiol. (2006) 290:R529-R535.
Ferrari, et al. "Targeting Ouabain- and Adducin-Dependent Mechanisms of Hypertension and Cardiovascular Remodeling as a Novel Pharmacological Approach", Medical Hypotheses (2007) 68:1307-1314.
Gandi, "Pathology" People's Health Press, 1st Edition, Sep. 2001 (with English Translation).
Gooz "Role of Metalloenzymes, Pathomechanism of Tissue Fibrosis" Science Daily, 2007.
Kuusniemi, et al. "Kidneys with heavy proteinuria show fibrosis, inflammation and oxidative stress, but no tubular phenotypic change" Kidney International 2005, 68:121-132.
Messerli, et al. "Essential Hypertension", Lancet (2007) 370:591-603.
Naderi, et al. "Primary Care Approach to Proteinuria" J. Am. Board Fam. Med. (2008), 21:569-574.
Ravera et al. "Importance of Blood Pressure Control in Chronic Kidney Disease" J. Am. Soc. Nephrol. (2006), 17:S98-S103.

*Primary Examiner* — Barbara P Badio
(74) *Attorney, Agent, or Firm* — Vedder Price P.C.; Thomas J. Kowalski; Deborah L. Lu

(57) ABSTRACT

Compound of formula (I), wherein the symbol have the meaning reported in the text; for preparing a medicament for the prevention and/or treatment of proteinuria, glomerulosclerosis or renal failure.

8 Claims, 6 Drawing Sheets

Proteinuria in wild-type and β-adducin knockout mice (11 months of age)

WT  2.43 ± 0.15 mg/6h, n=15
KO  1.62 ± 0.16 mg/24h, n=19, -30%, p<0.01

5-β, 14-β-ANDROSTANE DERIVATIVES USEFUL FOR THE TREATMENT OF PROTEINURIA, GLOMERULOSCLEROSIS AND RENAL FAILURE

CROSS REFERENCE TO RELATED APPLICATIONS

This application is a continuation of U.S. application Ser. No. 13/258,728 filed Sep. 22, 2011, which is a National Stage Entry of International Application Number PCT/EP2010/053571 Filed Mar. 18, 2010, which published as PCT Publication No. WO 2010/108855 on Sep. 30, 2010, which claims the benefit of European Application Number EP 09155834.6 filed Mar. 23, 2009.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to 17-β-(3-furyl) and (4-pyridazinyl)-5-β, 14-β-androstane derivatives, as useful agents for preparing a medicament for the prevention and treatment of proteinuria, glomerulosclerosis and renal failure.

BACKGROUND OF THE INVENTION

The term proteinuria derives from protein and urine and means the presence of an excess of serum proteins in the urine. Proteinuria may be a sign of renal (kidney) damage, since serum proteins are readily reabsorbed from urine, the presence of excess protein indicates either an insufficiency of absorption or impaired filtration. Proteinuria may be a feature of the following conditions: Nephrotic syndromes (i.e. intrinsic renal failure); toxic lesions of kidneys; Collagen vascular diseases (e.g., systemic lupus erythematosus); Glomerular diseases, such as membranous glomerulonephritis, focal segmental glomerulonephritis; Strenuous exercise; Stress; Diabetes mellitus; Drugs (e.g., NSAIDs, nicotine, penicillamine, gold and other heavy metals, ACE inhibitors, antibiotics, opiates especially heroin); Infections (e.g., HIV, syphilis, hepatitis, post-streptococcal infection); Aminoaciduria; Hypertensive nephrosclerosis; Interstitial nephritis and Glomerulosclerosis.

Glomerulosclerosis is a general term to describe scarring of the kidneys' tiny blood vessels, the glomeruli, the functional units in the kidney that filter urine from the blood. Many patients with glomerulosclerosis gradually get worse until their kidneys fail completely. This condition is called end-stage renal disease or ESRD. Patients with ESRD must go on dialysis (hemodialysis or peritoneal dialysis) to clean their blood or get a new kidney through transplantation.

The kidney glomerulus is a highly specialized structure that controls the plasma ultrafiltration of proteins. The specific cellular unit that ensures this control is the podocyte whose dysfunction is involved in a massive loss of proteins in the urine (proteinuria). It is well known that podocyte function is strictly under the control of specific proteins modulating the actin cytoskeleton. Mutations into the genes coding for such podocyte proteins are known to be associated with alterations of the glomerular membrane barrier and consequently with massive proteinuria and renal damage. Among these podocyte proteins, nephrin is a fundamental constituent of the slit pore membrane and modulates the cytoskeleton dynamics through the activation of a signal transduction pathway mediated by the tyrosin kinase Fyn which belongs to the Src family kinases (Trends Mol Med. 2007; 13: 396-403).

Adducin is a cytoskeletal protein involved in the regulation of the actin-spectrin dynamics in all the cells. Polymorphisms of the adducin genes have been demonstrated to be associated with hypertension and progression of the renal failure.

Experimental data indicate that α and β adducin are expressed into the glomerulus and their polymorphisms are involved in the altered expression of some podocyte proteins, proteinuria and progression of renal damage in animal models independently from their blood pressure. (J Hypertension 2003, 21 (Suppl. 4), abs 4C.4).

In details, the knockout mice for mutant β adducin, which are normotensive, show an increased expression of podocyte proteins, such as nephrin, synaptopodin, α-actinin, Fyn and ZO-1 and a reduction of urinary protein (FIG. 1), as compared with control mice, indicating a possible role of β adducin in the modulation of glomerular permeability independent from the blood pressure control.

In normotensive congenic NB rats, where the mutant β adducin gene from the parental hypertensive MHS strain (Q529R) has been introgressed into the normotensive MNS background (BBRC 2004; 324: 562-568), the expression of some podocyte proteins (nephrin, α-actinin, podocyn and ZO-1) measured in cultured podocytes have been found reduced (see FIG. 2) and associated to massive proteinuria and renal damage, as indicated by the immunofluorescence data (see FIG. 3) of the adult rats, as compared with the normotensive congenic NA strain carrying the wild type β adducin variant together with the α mutated one from the MHS strain. These findings are therefore suggestive of a pathological role of the mutant β adducin on kidney function, which is independent from blood pressure and is modulated by the α mutant variant.

The relevance of the experimental data obtained in the animal models for the human disease is supported by recent clinical findings showing that patients with IgA nephropathy have a faster progression toward end stage renal failure when carrying the β adducin mutation (CT+TT) in interaction with the α adducin mutated variant (Trp) (see FIG. 4).

Endogenous Ouabain (EO) has been widely recognized as a new hormone able to control blood pressure through different mechanisms and mainly through the modulation of the renal Na handling. High circulating levels of EO have been found associated with high blood pressure.

17-(3-Furyl) and (4-pyridaziny)-5-β, 14-β-androstane derivative are known compound.

EP0583578B 1 describes the beta-androstane derivatives claimed in the present application, a process for their preparation and their use for the treatment of cardiovascular disorders such as heart failure and hypertension.

EP0590271B 1 describes 17-aryl and 17-heterocyclyl-S-alpha, 14-β-androstane, androstene and androstadiene derivatives, a process for their preparation and their use for the treatment of cardiovascular disorders such as heart failure and hypertension.

EPO 590272 B 1 describes 17-aryl and 17-heterocyclyl-5-β, 14-β-androstane derivatives and their use for the treatment of cardiovascular disorders such as heart failure and hypertension.

WO2008148812 describes 17-β-(3-furyl) and (4-pyridazinyl)-5-beta, 14-beta-androstane derivatives and their use for treatment of restenosis after angioplastic or endoartherectomy, and diseases due to organ fibrosis.

None of the publications above mentioned disclose the use of the 5beta, 14beta-androstane derivatives for the prevention and/or treatment of proteinuria, glomerulosclerosis and renal failure.

It has now been found that 17-β-(3-furyl) and (4-pyridazinyl)-5-β, 14-β-androstane derivatives according to the present invention are useful agents for the prevention and treatment of proteinuria, glomerosclerosys and renal failure.

DESCRIPTION OF THE INVENTION

It is therefore an object of the present invention a compound of formula (I),

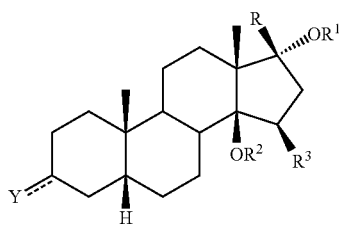

wherein:

the symbol ╌ represents a single or a double bond;

Y is oxygen or guanidinoimino when ╌ in position 3 is a double bond;

Y is hydroxy, $OR^4$ or $SR^4$, when ╌ in position 3 is a single bond and can have an alpha or beta configuration; R is an unsubstituted or substituted 3-furyl or 4-pyridazinyl group;

$R^1$ is hydrogen; methyl; ethyl or n-propyl substituted by OH or $NR^5R^6$;

$R^2$ is hydrogen or together to $R^3$ is a bond of an oxirane ring; $R^3$ is hydrogen or together to $R^2$ is a bond of an oxirane ring;

$R^4$ is hydrogen; methyl; C2-C6 alkyl or C3-C6 alkenyl or C2-C6 acyl, these alkyl, alkenyl and acyl groups being unsubstituted or substituted by a quaternary ammonium group or one or more $OR^7$, $NR^8R^9$, formyl, amidino, guanidinoimino or by $NR^8R^9$ and hydroxy;

$R^5$, $R^6$ are independently hydrogen; methyl; C2-C6 alkyl unsubstituted or substituted by one NR10R11, or NR10R11 and hydroxy, or $R^5$ and $R^6$ taken together with the nitrogen atom form an unsubstituted or substituted saturated or unsaturated penta- or hexa-monoheterocyclic ring, optionally containing another heteroatom chosen from oxygen or sulfur or nitrogen;

$R^7$ is hydrogen, methyl or C2-C4 alkyl, this alkyl being unsubstituted or substituted by one or more $NR^{10}R^{11}$ or by $NR^{10}R^{11}$ and hydroxy;

$R^8$, $R^9$ are independently hydrogen; methyl; C2-C6 alkyl or C3-C6 alkenyl, these alkyl and alkenyl groups being unsubstituted or substituted by one or more $NR^{10}R^{11}$, or $NR^{10}R^{11}$ and hydroxy, or $R^8$ and $R^9$ taken together with the nitrogen atom form an unsubstituted or substituted saturated or unsaturated penta- or hexa-monoheterocyclic ring, optionally containing another heteroatom chosen from oxygen or sulfur or nitrogen, or $R^8$ is hydrogen and $R^9$ is amidino; or $NR^8R^9$ represents propargylamino;

$R^{10}$, $R_{11}$ are independently hydrogen, C1-C6 alkyl, or $R^{10}$ and $R^{11}$, taken together with the nitrogen atom form a saturated or unsaturated penta- or hexa-monoheterocyclic ring;

Also included in this invention are pharmaceutically acceptable salts of (I), which retain the biological activity of the base and are derived from such known pharmaceutically acceptable acids such as hydrochloric, sulfuric, phosphoric, malic, tartaric, maleic, citric, methanesulfonic or benzoic acid;

The alkyl and alkenyl groups may be branched or straight chain groups;

The C1-C6 alkyl group is preferably a C1-C4 alkyl group, e.g. methyl, ethyl, n-propyl, isopropyl, n-butyl, sec-butyl;

The C2-C6 alkyl group is preferably a C2-C4 alkyl group, e.g. ethyl, n-propyl, isopropyl, n-butyl, sec-butyl;

The C3-C6 alkenyl group is preferably a C3-C4 alkenyl group, e.g. 2-propenyl, 2-butenyl;

The C2-C6 acyl is preferably a C2-C4 acyl group, e.g. acetyl, propionyl, butyryl;

The quaternary ammonium group is preferably a trimethylammonium- or a N-methylpyrrolidinium- or a N-methyl-piperidinium-group;

The $OR^7$ group is preferably hydroxy, 2-aminoethoxy, 3-aminopropoxy, 2-dimethylaminoethoxy, 2-diethylaminoethoxy, 3-dimethylaminopropoxy, 3-amino-2-hydroxypropoxy, 2,3-diaminopropoxy, 2-(1-pyrrolidinypethoxy, 3-(1-pyrrolidinyl)propoxy;

The $NR^5R^6$ group is preferably amino, methylamino, ethylamino, n-propylamino, dimethylamino, diethylamino, pyrrolidinyl, morpholino, piperazinyl, 1-imidazolyl, 2-aminoethylamino, 3-aminopropylamino;

The $NR^8R^9$ group is preferably amino, methylamino, ethylamino, n-propylamino, iso-propylamino, allylamino, propargylamino, dimethylamino, diethylamino, pyrrolidinyl, morpholino, piperazinyl, 1-imidazolyl, 1-guanidino, 2-aminoethylamino, 3-aminopropylamino, 2-(1-pyrrolidinyl) ethylamino, 3-(1-pyrrolidinyl)propylamino, 3-amino-2-hydroxypropylamino, 3-(1-pyrrolidinyl) 2-hydroxypropylamino, 2,3-diaminopropylamino, (2-(1-pyrrolidinyl) ethyl) methylamino; Preferred examples of specific compounds according to the present invention are:

17-β-(3-furyl)-5-β-androstane-3-β, 14-β, 17-α-triol;

3-β-(2-hydroxyethoxy)-17-β-(3-furyl)-5-β-androstane-14-β, 17-α-diol;

3-β-(2-aminoethoxy)-17-β-(3-furyl)-5-β-androstane-14-β, 17-α-diol;

3-β-(3-aminopropoxy)-17-β-(3-furyl)-5-β-androstane-14-β, 17-α-diol;

3-β-(2-methylaminoethoxy)-17-β-(3-furyl)-5-β-androstane-14-β, 17-α-diol;

3-β-(2-(1-pyrrolidinypethoxy)-17-β-(3-furyl)-5-β-androstane-14-β, 17-α-diol;

3-β-(2-(3-(1-pyrrolidinyl)propoxy)ethoxy)-17-β-(3-furyl)-5-β-androstane-14-β, 17-α-diol;

3-β-(3-(1-pyrrolidinyl)propoxy)-17-β-(3-furyl)-5-β-androstane-14-β, 17-α-diol;

3-β-(2-(1-imidazolypethoxy)-17-β-(3-furyl)-5-β-androstane-14-β, 17-α-diol; 3-β-(2-(2-imidazolin-2-yl)ethoxy)-17-β-(3-furyl)-5-β-androstane-14-β, 17-α-diol;
3-β-(2-(2-amidino)ethoxy)-17-β-(3-furyl)-5-β-androstane-14-β, 17-α-diol;
3-β-(2-(2-(1-pyrrolidinyl)ethoxy)ethoxy)-17-β-(3-furyl)-5-β-androstane-14-β, 17-α-diol;
3-β-(2-guanidinoethoxy)-17-β-(3-furyl)5-β-androstane-14-β, 17-α-diol;
3-β-(3-guanidinopropoxy)-17-β-(3-furyl)-5-β-androstane-14-β, 17-α-diol;
3-β-(3-amino-2-hydroxypropoxy)-17-β-(3-furyl)-5-β-androstane-14-β, 17-α-diol;
3-β-(2,3-diaminopropoxy)-17-β-(3-furyl)5-β-androstane-14-β, 17-α-diol; 17-β-(3-furyl)-17-α-methoxy-5-β-androstane-3-β, 14-β-diol;
17-β-(3-furyl)-17-α-(2-(1-pyrrolidinyl)ethoxy)-5-β-androstane-3-β, 14-β-diol;
17-β-(3-furyl)-17-α-(3-aminopropoxy)-5-β-androstane-3-β, 14-β-diol; 3-β-(2-(1-pyrrolidinyl)ethoxy)-17-β-(3-furyl)-17-α-methoxy-5-β-androstan-14-β-ol;
3-β, 17-α-bis(2-(1-pyrrolidinyl)ethoxy)-17-β-(3-furyl)-5-β-androstan-14-β-ol;
3-β, 17-α-bis(3-aminopropoxy)-17-β-(3-furyl)-5-β-androstan-14-β-ol;
14-β, 17-α-dihydroxy-17-β-(3-furyl)-5-β-androstan-3-one;
3-guanidinoimino-17-β-(3-furyl)-5-β-androstane-14-β, 17-α-diol;
17-β-(4-pyridazinyl)-5-β-androstane-3-β, 14-β, 17-α-triol;
3-β-(2-hydroxyethoxy)-17-β-(4-pyridazinyl)5-β-androstane-14-β, 17-α-diol;
3-β-(3-aminopropoxy)-17-β-(4-pyridazinyl)-5-β-androstane-14-β, 17-α-diol;
3-β-(2-(1-pyrrolidinyl)ethoxy)-17-β-(4-pyridazinyl)-5-β-androstane-14-β, 17-α-diol;
3-β-(3-(1-pyrrolidinyl)propoxy)-17-β-(4-pyridazinyl)-5-β-androstane-14-β, 17-α-diol;
17-β-(4-pyridazinyl)-17-α-(3-aminopropoxy)-5-β-androstane-3-β, 14-β-diol; 3-β-(2-(1-pyrrolidinyl)ethoxy)-17-β-(4-pyridazinyl)-17-α-methoxy-5-β-androstan-14-β-ol;
3-β-(2-(1-pyrrolidinyl)ethoxy)-17-β-(4-pyridazinyl)-17-α-(3-amino-propoxy)-5-β-androstan-14-β-ol;
14-β, 17-α-dihydroxy-17-β-(4-pyridazinyl)-5-β-androstan-3-one; 3-guanidinoimino-17-β-(4-pyridazinyl)-5-β-androstane-14-β, 17-α-diol;
14-β, 15-β-epoxy-17-β-(3-furyl)-5-β-androstane-3-β, 17-α-diol;
3-β-(2-hydroxyethoxy)-14-β, 15-β-epoxy-17-β-(3-furyl)-5-β-androstan-17-α-ol;
3-β-(3-aminopropoxy)-14-β, 15-β-epoxy-17-β-(3-furyl)-5-β-androstan-17-α-ol;
3-β-(2-(1-pyrrolidinyl)ethoxy)-14-β, 15-β-epoxy-17-β-(3-furyl)-5-β-androstan-17-α-ol;
3-β-(3-(1-pyrrolidinyl)propoxy)-14-β, 15-β-epoxy-17-β-(3-furyl)-5-β-androstan-17-α-ol;
3-β-(2-(1-pyrrolidinyl)ethoxy)-17-β-(3-furyl)-17-α-methoxy-14-β, 15-β-epoxy-5-β-androstane;
17-α-hydroxy-17-β-(3-furyl)-14-β, 15-β-epoxy-5-β-androstan-3-one;
3-guanidinoimino-17-β-(3-furyl)-14-β, 15-β-epoxy-5-β-androstan-17-α-ol;
14-β, 15-β-epoxy-17-β-(4-pyridazinyl)-5-β-androstane-3-β, 17-α-diol;
and the 3 alpha derivatives of the above identified 3-β derivatives and also the corresponding 3 alpha and 3-β thioderivatives where Y=S;
for use as antiproteuremic agent.

The most preferred example of specific compound according to the present invention is 17-β-(3-(3-Furyl)-5-β-androstane-3-β, 14-β, 17-α-triol, in the following mentioned as "rostafuroxin" or "PST 2238".

It is a further object of the present a compound of formula (I) for use as antiglomerosclerotic agent. It is a further object of the present a compound of formula (I) for use as anti renal failure agent.

It is a further object of the present invention the use of a compound of formula (I) for the preparation of a medicament for the prevention or treatment of proteinuria, glomerulosclerosis and renal failure.

It is a further object of the present invention a method of treating a mammal suffering from proteinuria, glomerulosclerosis or renal failure, comprising administering a therapeutically effective amount of a compound of formula (I). The term "therapeutically effective amount" as used herein refers to an amount of a therapeutic agent needed to treat, ameliorate a targeted disease or condition, or to exhibit a detectable therapeutic effect.

For any compound, the therapeutically effective dose can be estimated initially either in cell culture assays or in animal models, usually mice, rabbits, dogs, or pigs.

The animal model may also be used to determine the appropriate concentration range and route of administration. Such information can then be used to determine useful doses and routes for administration in humans. The precise effective amount for a human subject will depend upon the severity of the disease state, general health of the subject, age, weight, and gender of the subject, diet, time and frequency of administration, drug combination (s), reaction sensitivities, and tolerance/response to therapy. This amount can be determined by routine experimentation and is within the judgement of the clinician. Generally, an effective dose per day will be from 0.05 mg to 20 mg, preferably 0.5 mg to 15 mg, most preferably 5 mg to 10 mg.

Dosage treatment may be a single dose schedule or a multiple dose schedule, according to the physician judgement. Compositions may be administered individually to a patient or may be administered in combination with other agents, drugs or hormones.

The medicament may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity.

Suitable carriers may be large, slowly metabolised macromolecules such as proteins, polysaccharides, polylactic acids, polyglycolic acids, polymeric amino acids, amino acid copolymers and inactive virus particles.

A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The medicament of this invention may be administered by any number of routes including, but not limited to, oral, intravenous, intramuscular, intra-arterial, intramedullary, intrathecal, intraventricular, transdermal or transcutaneous applications, subcutaneous, intraperitoneal, intranasal, enteral, topical, sublingual, rectal means or locally on the diseased tissue after surgical operation. The compound of the invention may also be applied (coated) on the stent even incorporated into a controlled-release matrix.

BRIEF DESCRIPTION OF THE DRAWINGS

FIG. 2 represents the amount of podocyte proteins (nephrin, α-actinin, ZO-1, podocin, α-adducin and actin) expressed in cultured podocytes obtained from neonatal (<10-day-old) rats from the congenic NB and NA strains. Podocyte proteins were quantified on podocyte extracts by Western blotting with appropriate antibodies (see the representative traces on the top of bars). Data are reported as meant sem of several experiments ranging from 4 to 24 for each strain. Statistical analysis was carried out by t Student's test. The figure shows that the amounts of Nephrin, α-Actinin, ZO-1, Podocin and α-Adducin are significantly reduced in podocytes from NB normotensive rats carrying the mutant β-adducin as compared to NA controls carrying the wild type variant, while the housekeeper protein actin is similar.

The following non-limiting examples further illustrate the invention.

EXAMPLE 1

To test the activity of the compound of the invention for the prevention of loss of podocyte proteins, congenic NB rats carrying the beta adducin mutation (Tripodi G. et at Effect of Add1 gene transfer on blood pressure in reciprocal congenic strains of Milan rats. BBRC 2004; 324: 562-568) were used. Said NB rats are non-hypertensive rats and are available at Prassis Research Institute, Sigma-tau, Italy.

NB rats of 7 to 10 days of age were used for podocyte isolation and culture. Podocytes from NB rats were incubated for 5 days without (NB control, n=4) and with Rostafuroxin at $10^{-9}$M (NB n=5). Podocyte proteins were quantified at the end of the 5 days of incubation by Western blotting. The quantification by Western blot was replicated two to three times for each podocyte marker. Tables IA and IB show the final number of podocyte samples analyzed for each condition, as mean values of the replicates (NB control, n=4; NB+Rostafuroxin, n=5). The densitometric analysis was quantified as optical density, in arbitrary units.

Podocyte Isolation and Protein Quantification in Cultured Podocytes

Glomeruli were isolated from NB kidneys by sieving and further manually purification. Glomeruli were then seeded in culture flasks (Corning, Sigma-Aldrich, Milan, Italy), pre-coated with collagen type IV (Sigma-Aldrich) at 37° C. in 5% $CO_2$ atmosphere. On days 4 to 5, podocyte growth started and, by day 8, glomeruli were detached using trypsin-EDTA. Second passage podocytes, which resulted in >90% pure as judged by light microscopy inspection, were seeded on flasks and chamber slides. Podocyte protein quantification (10 µg protein/lane) was performed by Western blotting technique by using specific antibodies against nephrin, podocin, ZO-1, adducin, synaptopodin and actin.

Figure 1:
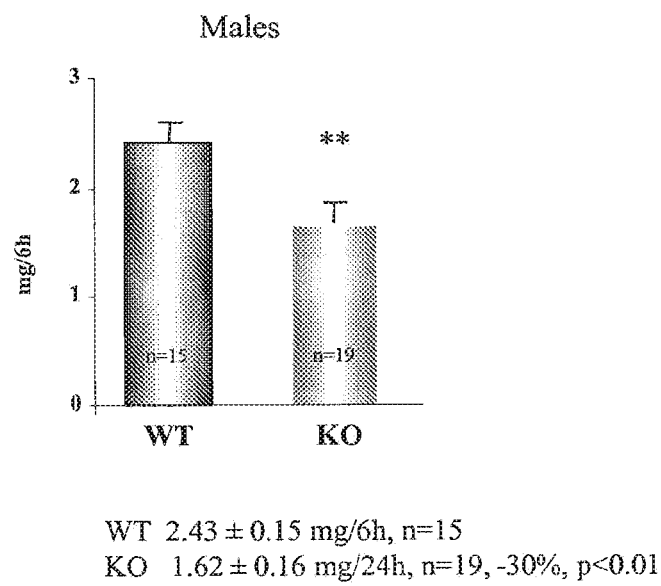
FIG. 1 represents the level of urinary protein excretion (mg/6 h) in mice carrying the knockout (KO) of the beta adducin as compared with the wild type (WT) controls. Male mice were 11 month-olds and urinary protein excretion was measured on urine collected for 6 hours from each mouse housed in metabolic cage. Data are mean±sem of 15 WT and 19 KO mice. Statistical analysis was carried out by t Student's test. The figure shows that the 6 hour-urinary protein excretion was significantly decreased (by 30%) in KO mice for beta adducin as compared to WT controls.
Figure 2:
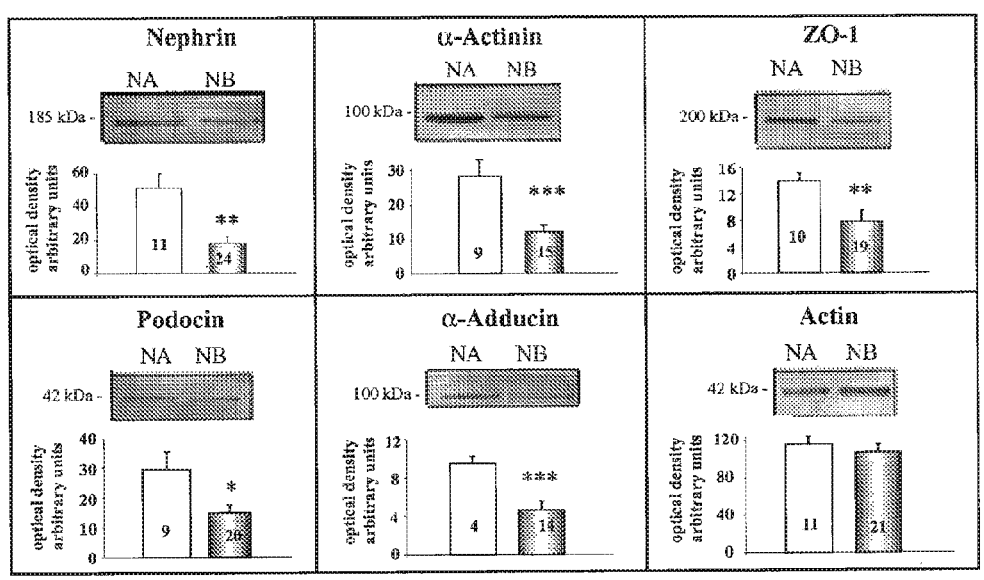
Figure 3:
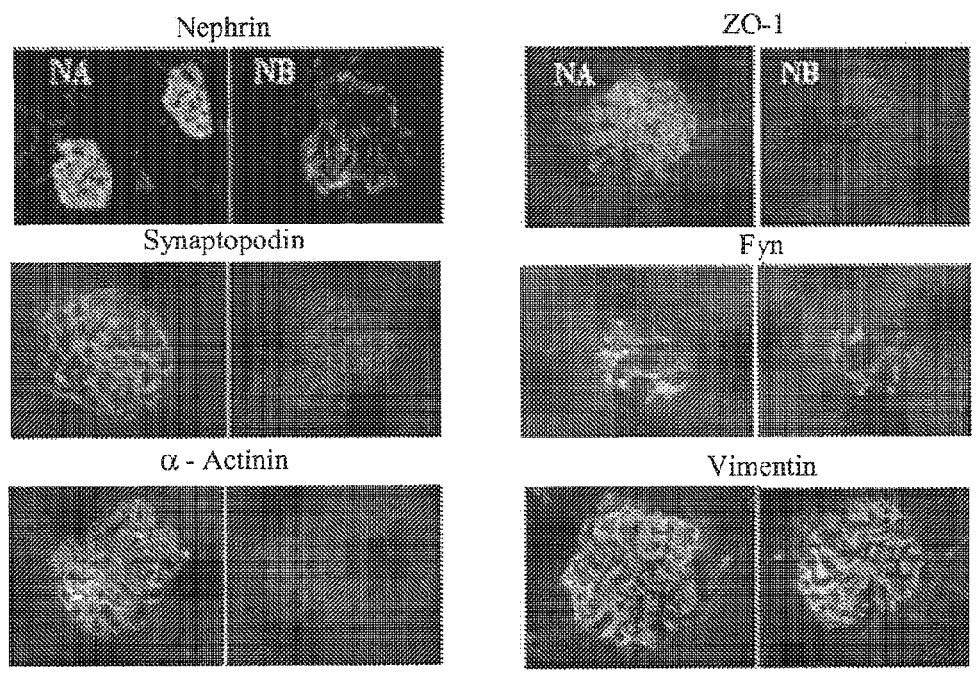
FIG. 3 represents the expression of some podocyte proteins (Nephrin, Synaptopodin, α-Actinin, ZO-1, Fyn and Vimentin) as detectable by immunofluorescence in renal glomeruli from NB normotensive rats carrying the mutant β-adducin as compared to NA controls carrying the wild type variant. The figure shows that the expression of these proteins is drastically reduced in NB as compared to NA rats, while Vimentin, a microfilament localized in the podocyte cell body, is normally expressed in the two strains.
Figure 4:
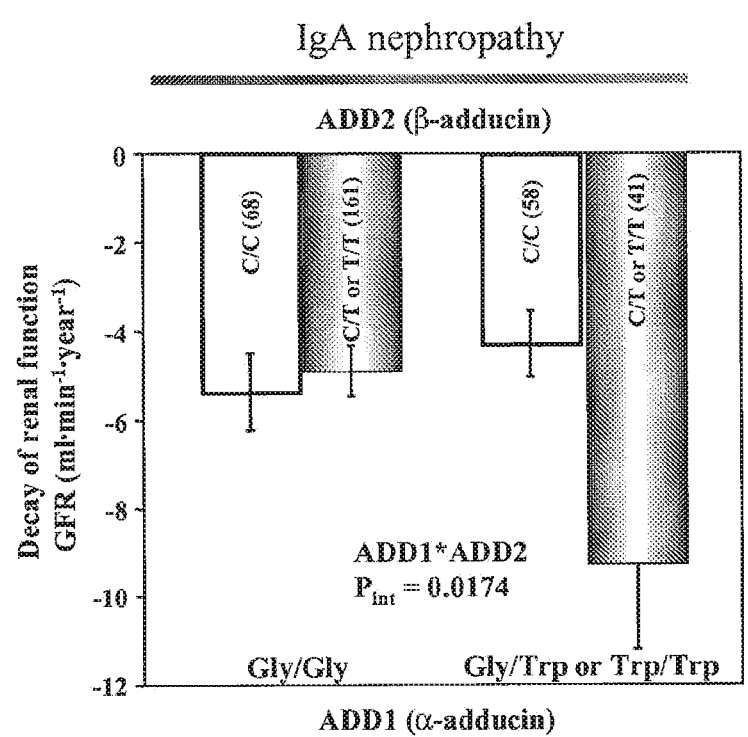
FIG. 4 shows the progression of renal failure evaluated as the decay of glomerular filtration rate (GFR) over time (ml.min^.year 1) in patients affected by IgA nephropathy subdivided in 4 groups according to α-adducin (ADD1, Gly460Tyr) and β-adducin (ADD2, C399T) genotypes. The interaction between the two genes on the rate of decay was found significant.
Figure 5:
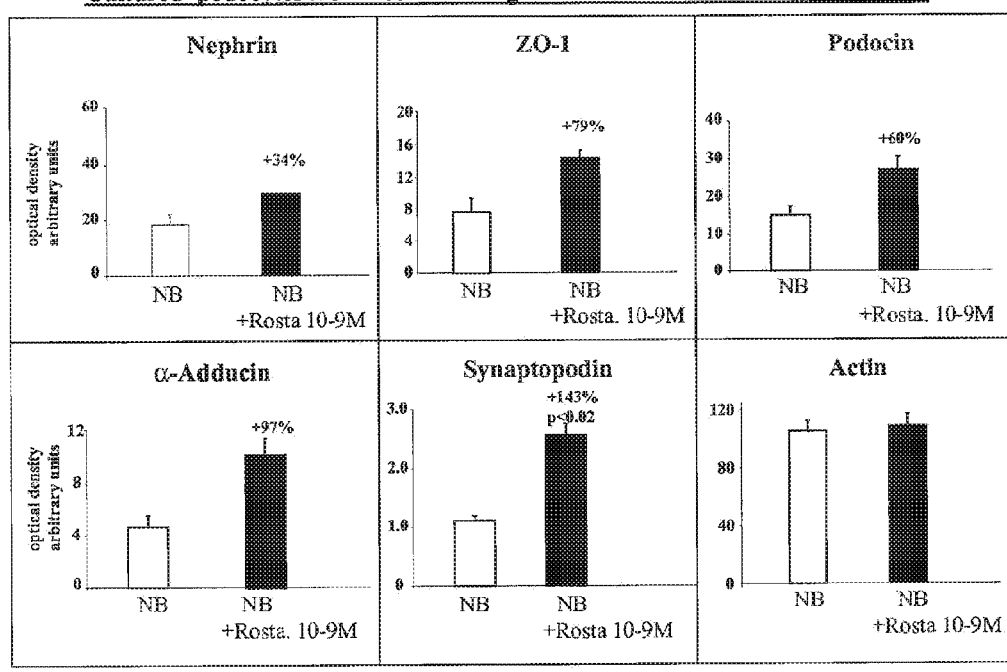
FIG. 5 represents the amount of podocyte proteins (nephrin, ZO-1, podocin, α-adducin, synaptopodin and actin) expressed in cultured podocytes obtained from neonatal (<10-day-old) rats from the congenic NB strain and incubated for 5 days with or without Rostafuroxin $10^{-9}$M. Podocyte proteins were quantified on podocyte extracts by Western blotting with appropriate antibodies. Data are reported as mean±sem of several experiments. Statistical analysis was carried out by t Student's test. The figure shows that the amounts of Nephrin, ZO-1, Podocin, α-Adducin and Synaptopodin, but not Actin, are increased in podocytes cultured in the presence of $10^{-9}$M Rostafuroxin.

The results obtained are reported in the following Table 1A, 1B and in FIG. 5

TABLE 1A

| Podocyte Marker | Sample number | NB Controls | Sample number | NB + Rostafuroxin | % vs. Ctrl. |
|---|---|---|---|---|---|
| Nephrin | 1 | 19.21-19.27 | 1 | 24.53 | |
|  | — | — | 2 | 27.06 | |
| mean | | 19.24 | | 25.8 | +34 |
| ZO-1 | 1 | 7.69-7.68-5.38-1.16 | 1 | 17.3-17.8 | |
|  |  |  | 2 | 6.38-7.5 | |
|  | 2 |  | 3 | 8.73-13.33-15.79 | |

TABLE 1A-continued

| Podocyte Marker | Sample number | NB Controls | Sample number | NB + Rostafuroxin | % vs. Ctrl. |
|---|---|---|---|---|---|
| | 3 | | 4 | 11.67-16.05-19.98 | |
| | 4 | | 5 | 12.78-19.06-20.13 | |
| Mean ± sem | | 7.69 ± 1.03 | | 14.36 ± 1.3 | +86 p < 0.001 |
| Podocin | 1 | 18.32-14.8-4.6-4.85 | 1 | 23.4-49.06 | |
| | | | 2 | 13.3-19.07 | |
| | 2 | 11.9-14.38-12.23 | 3 | 16.81-18.63-21.42 | |
| | 3 | 14.15-16.57-21 | 4 | 18.78-23.84-36.51 | |
| | 4 | 19.63-22.76-20.3 | 5 | 21.23-23.65-27.62 | |
| Mean ± sem | | 15.03 ± 1.58 | | 24.13 ± 2.6 | +60 p < 0.01 |

TABLE 1B

| Podocyte Marker | Sample number | NB Controls | Sample number | NB + Rostafuroxin | % vs. Ctrl. |
|---|---|---|---|---|---|
| α-Adducin | 1 | 4.42-2.10 | 1 | 22.23 | |
| | | | 2 | 6.06 | |
| | 2 | 4.38-6.02 | 3 | 5.70-6.77 | |
| | 3 | 5.17-3.91 | 4 | 8.06-7.53 | |
| | 4 | 4.47-6.75 | 5 | 9.33-7.07 | |
| Mean ± sem | | 4.65 ± 0.49 | | 9.09 ± 1.9 | +95 p < 0.001 |
| Synaptopodin | 1 | 1.1 | 1 | 2.7 | |
| | | | 2 | 2.51 | |
| | 2 | 1.61 | 3 | 4.29 | |
| | 3 | 0.912 | 4 | 1.43 | |
| | 4 | 0.79 | 5 | 2.56 | |
| Mean ± sem | | 1.10 ± 0.18 | | 2.70 ± 0.45 | +143 p < 0.02 |
| Actin | 1 | 64.3-95-90-88.5 | 1 | 130.5 | |
| | | | 2 | 115-87.5-140.4 | |
| | 2 | 97.3-94.8-100-97 | 3 | 111-98-98.2-81.2 | |
| | 3 | 120.0-90.4-94-109.9 | 4 | 86.2-101.2-101-144.2 | |
| | 4 | 99.4-92.4-85.4-160.9 | 5 | 87.7-108-103-91.6 | |
| Mean ± sem | | 100.5 ± 4.53 | | 105.3 ± 4.75 | ns |

The results obtained indicate that the compound of the invention is able to antagonize the podocyte protein loss induced by—beta adducin mutation thus favouring the correct function of the glomerular filtration barrier and reducing proteinuria in a normotensive experimental model.

EXAMPLE 2

To test the activity of the compound of the invention for the prevention of proteinuria and loss of renal glomerular proteins, rats chronically infused with ouabain (OS rats) or saline (Control rats) were utilized.

Two groups of 2-month-old OS rats (n=8 each) were orally treated by gavage with vehicle (Methocel 0.5%) or Rostafuroxin (100 μg/kg) for 8 weeks. One group of saline infused rats was used as control. After this period, systolic blood pressure and urinary protein excretion was measured in the three groups. The animals of the three groups were then sacrificed for nephrin quantification from renal cortex microsomes by Western blotting.

Ouabain Infusion

Three week-old male Sprague-Dawley rats (Harlan, Ind.), weighing 100-110 g, were subcutaneously implanted with osmotic mini-pumps, releasing either 15 μg/kg/day of ouabain (OS rats, n=16) for 14 weeks or sterile saline (CS rats, n=8) (Ferrari P. et al. J. Pharmacol Exp. Ther. 1998; 285: 83-94). At the 6th week of ouabain infusion, OS rats were randomly assigned to two groups (n=8 each): the first (OS treated) received Rostafuroxin orally at 100 μg/kg/day, suspended in 0.5% w/v Methocel, and the second group (controls) only vehicle. Systolic blood pressure (SBP) and heart rate (HR) were measured weekly in conscious rats by tail-cuff plethysmography (BP recorder, U. Basile, Italy).

Biochemical Assays for the Measurement of Urinary Parameters

Urinary parameters were measured in conscious OS and control rats at the 12th week of treatment. Rats were housed in individual metabolic cages and acclimated for one day. 24-hours urines collection started at 9 a.m. During urine collection, rats had free access to water and food. After centrifugation (4500 rpm for 20 min; Varifuge 3.2 RS, Haereus Instruments, AHSI, Milan, Italy), rat urines were analyzed for the urinary volume (ml), quantified by weighing the urinary reservoir on a precision Mettler balance; urinary pH (pHM83, Radiometer, Copenhagen) and total urinary protein excretion (mg/24 h), measured with a standard total protein Kit (Sentinel Diagnostics, Milan, Italy). The animals of the three groups were then sacrificed, renal cortical microsomes were prepared from each rat and nephrin, the key protein of the slit diaphragm membrane, was quantified by Western blotting. Samples were separated by SDS-polyacrylamide gel electrophoresis, blotted and overnight incubated at 4° C. with specific primary antibodies (anti-nephrin from Santa Cruz; anti-actin from Sigma-Aldrich), followed by 1 h incubation with fluorescent secondary antibodies (Alexa Fluor), then analyzed and quantified by Odyssey Infrared Imaging detection system (LI-COR Biosciences). Nephrin quantification is expressed as optical density, arbitrary units.

Figure 6:
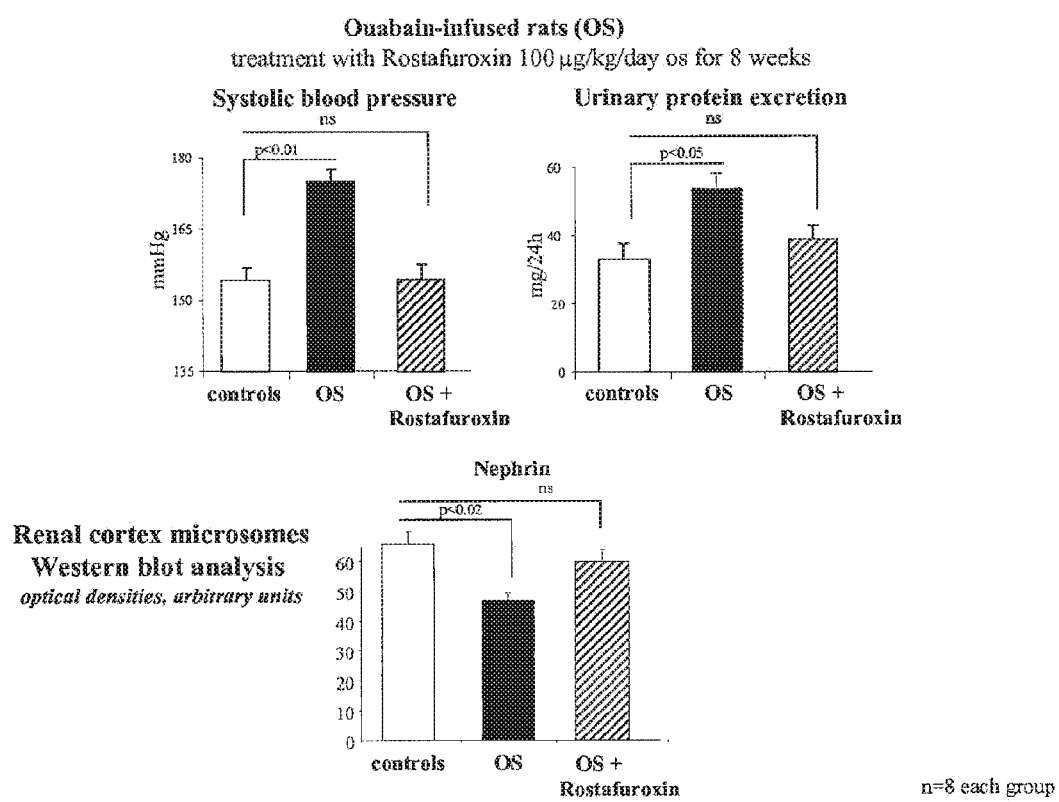
FIG. 6 represents the systolic blood pressure (SBP), urinary protein excretion and amount of Nephrin from renal cortex of rats chronically infused with ouabain (OS) and treated with vehicle as compared either to control saline infused rats or OS rats orally treated for 8 weeks with Rostafuroxin 100 µg/kg/day. Data are reported as mean±sem of 8 rats for each group. Statistical analysis was carried out by t Student's test. The figure shows that Rostafuroxin significantly reduced SBP and urinary protein excretion while it increased Nephrin expression in OS rats, thus antagonizing the renal effects of ouabain.

The results obtained are reported in the following Tables 2A; 2B; 2C; and FIG. 6.

TABLE 2A

| Saline control | | | |
|---|---|---|---|
| Saline control | Systolic blood pressure mmHg | Proteinuria mg/24 h | Nephrin optical density arbitrary units |
| 1 | 140 | 31.63 | 64.51 |
| 2 | 150 | 45.06 | 64.3 |
| 3 | 150 | 28.2 | 79.92 |
| 4 | 145 | 51.6 | 52.88 |
| 5 | 135 | 29.16 | 66.06 |
| 6 | 145 | 21.95 | 58.92 |
| 7 | 150 | 25.44 | 45.91 |
| 8 | 140 | 45.44 | — |
| mean ± sem | 144 ± 1.2, n = 8 | 34.9 ± 3.8, n = 8 | 61.8 ± 4, n = 7 |

TABLE 2B

Ouabain-infused rats (OS): effect of treatment with methocel (vehicle)

| OS rats | Systolic blood Pressure mmHg | Proteinuria mg/24 h | Nephrin optical density arbitrary units |
|---|---|---|---|
| 1 | 170 | 35.41 | 51.4 |
| 2 | 180 | 79.3 | 49.7 |
| 3 | 170 | 42.3 | 35.9 |
| 4 | 170 | 37.8 | 41.9 |
| 5 | 165 | 57.07 | 47.0 |
| 6 | 160 | 45.2 | 52.3 |
| 7 | 175 | 47.19 | 44.3 |
| 8 | 170 | 60.3 | 52.2 |
| mean ± sem | 170 ± 2.1, n = 8 $p < 0.01$ vs. Saline | 50.6 ± 5.1, n = 8 $p < 0.05$ vs. Saline | 46.7 ± 2.1, n = 8 $p < 0.02$ vs. Saline |

TABLE 2C

Ouabain-infused rats (OS): effect of treatment with 100 μg/kg os Rostafuroxin

| OS treated with Rostafuroxin | Systolic blood Pressure mmHg | Proteinuria mg/24 h | Nephrin optical density arbitrary units |
|---|---|---|---|
| 1 | 135 | 53.07 | 64.7 |
| 2 | 150 | 20.14 | 54.8 |
| 3 | 155 | 55.34 | 51.4 |
| 4 | 145 | 29.02 | 50.8 |
| 5 | 155 | 39.7 | 76.1 |
| 6 | 145 | 40.68 | 57.4 |
| 7 | 155 | 20.85 | 48.8 |
| 8 | 150 | 48.88 | 53.8 |
| mean ± sem | 148.8 ± 2.5, n = 8 ns vs. Saline | 38.5 ± 4.9, n = 8 ns vs. Saline | 57.3 ± 3.1, n = 8 ns vs. Saline |

The results obtained indicate that the compound of the invention is able to antagonize the pathological effects of ouabain on blood pressure, urinary protein excretion and glomerular protein loss thus lowering blood pressure, re-establishing the glomerular nephrin expression and reducing proteinuria.

The invention claimed is:

1. A method for treating proteinuria, comprising the step of administering to a normotensive patient in need thereof a therapeutically effective amount of a compound of formula (I),

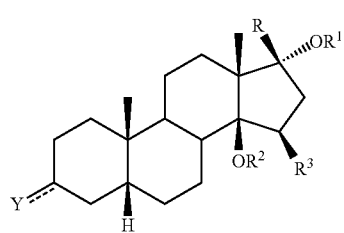

(I)

wherein:

the symbol --- represents a single bond;

Y is $OR^4$ and has an alpha or a beta configuration;

R is 3-furyl;

$R^1$ is hydrogen;

$R^2$ is hydrogen;

$R^3$ is hydrogen;

$R^4$ is hydrogen.

2. The method according to claim 1, wherein the compound is administered in a dose of from 0.05 mg to 20 mg per day.

3. The method according to claim 2, wherein the compound is administered in a dose of from 0.5 mg to 15 mg.

4. The method according to claim 3, wherein the compound is administered in a dose of from 5 mg to 10 mg.

5. The method according to claim 4, wherein the compound is administered) in a single dose schedule.

6. The method according to claim 4, wherein the compound is administered in a multiple dose schedule.

7. The method according to claim 1, wherein the compound is administered to the patient orally, intravenously, intramuscularly, intra-arterially, intramedullary, intrathecally, intraventricularly, transdermally, transcutaneously, subcutaneously, intraperitoneally, intranasally, enterally, topically, sublingually or rectally.

8. A method of antagonizing podocyte protein loss in a normotensive patient in need thereof, which comprises administering to said patient a therapeutically effective amount of a compound of formula (I),

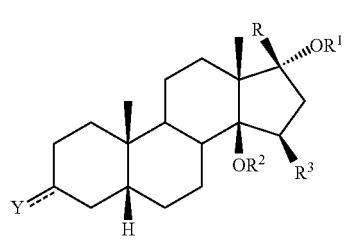

(I)

wherein:

the symbol --- represents a single bond;

Y is $OR^4$ and has an alpha or a beta configuration;

R is 3-furyl;

$R^1$ is hydrogen;

$R^2$ is hydrogen;

$R^3$ is hydrogen;

$R^4$ is hydrogen.

* * * * *

UNITED STATES PATENT AND TRADEMARK OFFICE
CERTIFICATE OF CORRECTION

PATENT NO. : 9,868,757 B2
APPLICATION NO. : 14/931083
DATED : January 16, 2018
INVENTOR(S) : Patrizia Ferrari, Giuseppe Bianchi and Mara Ferrandi Page 1 of 1

It is certified that error appears in the above-identified patent and that said Letters Patent is hereby corrected as shown below:

On the Title Page

Item (63) Related U.S. Application Data
Please change: "Continuation of application No. 13/258,728, filed as application No. PCT/EP2010/053571 on Mar. 18, 2010, now abandoned."
To: --Continuation of application No. 13/258,728 filed Sept. 22, 2011, now abandoned, which is a National Stage Entry of PCT/EP2010/053571 filed Mar. 18, 2010.--

Signed and Sealed this
Nineteenth Day of June, 2018

Andrei Iancu
*Director of the United States Patent and Trademark Office*